United States Patent [19]

Clark et al.

[11] Patent Number: 5,726,197
[45] Date of Patent: Mar. 10, 1998

[54] ISOINDOLINYL DERIVATIVES

[75] Inventors: Robin D. Clark, Palo Alto, Calif.; Michael Spedding, Paris, France

[73] Assignee: Syntex (U.S.A.) Inc., Palo Alto, Calif.

[21] Appl. No.: 971,015

[22] Filed: Nov. 2, 1992

[51] Int. Cl.[6] .......... C07D 417/04; A61K 31/425
[52] U.S. Cl. .......... 514/387; 514/370; 514/377; 548/181; 548/233; 548/312.1
[58] Field of Search .......... 548/181, 233, 548/312.1; 514/370, 377, 387

[56] References Cited

U.S. PATENT DOCUMENTS 4,777,181 10/1988 Cohnen et al. .......... 514/392
4,918,083 4/1990 Berge et al. .......... 514/323

OTHER PUBLICATIONS

Affinity of 2-(Tetrahydroisoquinolin-2-ylmethyl)-and 2-(Isoindolin-2-ylmethyl)imidazolines for α-Adrenoceptors. Differential Affinity of Imidazolines for the [3H]Idazoxan-Labeled α₂-Adrenoceptor vs the [3H]Yohimbine-Labeled Site[1], by Clark, et al., *Journal of Medicinal Chemistry*, 1990, vol. 33, No. 2, pp. 596–600.

Novel $\alpha_2$–adrenoceptor antagonists show selectivity for $\alpha_{2A}$– and $\alpha_{2B}$–adrenoceptor subtypes, by Young, et al., *European Journal of Pharmacology*, vol. 168 (1989) pp. 381–386.

Gawley, J. Org. Chem. 53, 5381 (1988).

*Primary Examiner*—Robert Gerstl
*Attorney, Agent, or Firm*—Heller Ehrman White & McAuliffe

[57] ABSTRACT

Compounds of the Formula:

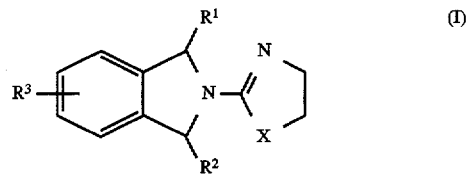

wherein:
- $R^1$ and $R^2$ are independently hydrogen or lower alkyl;
- $R^3$ is hydrogen, lower alkyl, lower alkoxy, hydroxy, halo, optionally substituted phenyl, amino, nitro or trifluoromethyl; and
- X is —NH—, —O— or —S—;

and the pharmaceutically acceptable salts thereof exhibit high affinity and selectivity for imidazoline receptors, and are are particularly useful for modification of the female reproductive cycle.

18 Claims, No Drawings

ISOINDOLINYL DERIVATIVES

FIELD OF THE INVENTION

Many compounds with $\alpha_2$-adrenergic antagonist activity have been discovered. Such compounds exert a wide range of physiological effects, and have been found to be useful for the treatment of diverse disease states such as lowering of blood pressure in hypertensive mammals, treatment of irritable bowel syndrome, inhibition of platelet aggregation, treatment of hypoglycemia, palliation of diabetes, lowering of intraocular pressure, depression, impotence, sexual dysfunction, and for a variety of vascular disorders (see, for example, McGrath, Brown and Wilson, *Med. Res. Rev.*, Vol. 9, pp 407–533 (1989)).

However, over the last several years it has become clear that some $\alpha_2$-adrenergic antagonists, for example idazoxan, also recognize an additional class or classes of receptor, known variously as imidazoline receptors or imidazole receptors (IM), or IM-preferring receptors, (see, for example, *Gastroenterology*, Vol. 86, pp 120–8 (1984), *Br. J. Pharmacol*, Vol 104, pp 258–262 (1991), *European J. Pharmacol*, 199, pp 243–245 (1991), *European J. Pharmacol*, 176, pp 97–101 (1990)). Such receptors (referred to herein as imidazoline receptors) differ from $\alpha_2$-adrenergic receptors with respect to distribution in the brain, kidney, etc, and also have very different affinities for different compounds. We have found that certain compounds, some of which are not themselves imidazolines, demonstrate high affinity and selectivity for imidazoline receptors. It is apparent that the treatment of some disease states usually associated with $\alpha_2$-adrenoceptor antagonist action is in fact related to a compound's interaction with imidazoline receptor sites.

It is evident that it would be desirable to have compounds that are selective and with high affinity for imidazoline receptor sites, but with little or no $\alpha_2$-adrenergic antagonist action. In this manner, medicaments with more specific activity for physiological effects associated with the imidazoline receptor could be developed, keeping unwanted effects due to $\alpha_2$-adrenergic antagonist action to a minimum.

Surprisingly, we have discovered a class of compounds with this desired spectrum of activity. Because of the exceptionally high selectivity and affinity of the compounds of our invention for the imidazoline site, they are also useful as an assay tool for the detection of the presence of such sites in, for example, the brain, the kidney, etc. As a consequence of the high affinity and selectivity for imidazoline sites, the compounds are considered to be useful for the treatment of various diseases, including cerebral ischemia, hypertension, alleviation of excessive intraocular pressure, parkinsonian disorders, eating disorders, modulation of seasonal affective disorders, panic disorders, urinary incontinence, diuresis, fertility disorders (including the treatment of infertility by, for example, in vitro fertilization, and use in antifertility), sexual dysfunction, impotence, postnatal depression, mild stress-induced amenorrhoea, and galactorrhoea. The compounds of Formula (I) are particularly useful for modification of the female reproductive cycle.

The compounds of the invention are various isoindolinyl derivatives, substituted at the 2-position by thiazoline, oxazoline or imidazoline.

RELATED DISCLOSURES

The compounds of this invention are various isoindolinyl derivatives. Compounds somewhat structurally related are described in U.S. Pat. Nos. 4,777,181 and 4,918,083. *J. Med. Chem.*, Vol. 33, pp 596–600 (1990), and *Eur. J. Pharmacol.*, 168, pp 381–386 (1989). However, none of the compounds disclosed therein have the exceptionally high selectivity and affinity for the imidazoline receptor site demonstrated by the compounds of our invention.

SUMMARY OF THE INVENTION

One aspect of the invention concerns compounds represented by the formula:

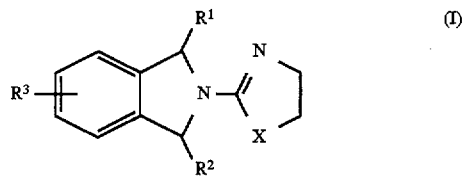

wherein:
$R^1$ and $R^2$ are independently hydrogen or lower alkyl;
$R^3$ is hydrogen, lower alkyl, lower alkoxy, hydroxy, halo, optionally substituted phenyl, amino, nitro or trifluoromethyl; and
X is —NH—, —O— or —S—;
and the pharmaceutically acceptable salts thereof.

In another aspect, the invention relates to pharmaceutical compositions containing a therapeutically effective amount of a compound of Formula (I), or a pharmaceutically acceptable salt thereof, in admixture with one or more pharmaceutically acceptable, non-toxic carriers.

In yet another aspect, the invention relates to a method for treating a mammal having a disease state which is alleviable by treatment with a compound having high selectivity and affinity for the imidazoline receptor site, especially where the disease state is cerebral ischemia, hypertension, excessive intraocular pressure, parkinsonian disorders, eating disorders, seasonal affective disorders, panic disorders, urinary incontinence, diuresis, fertility disorders (including the treatment of infertility by, for example, in vitro fertilization, and use in antifertility), sexual dysfunction, impotence, postnatal depression, mild stress-induced amenorrhoea, and galactorrhoea, by administering to a mammal in need thereof a therapeutically effective amount of a compound of Formula (I), or a pharmaceutically acceptable salt thereof.

In a further aspect, the invention relates to a method of determining the presence of imidazoline receptor sites in mammalian tissue, especially human tissue.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Halo" denotes fluoro, chloro, bromo, or iodo, unless otherwise indicated.

"Phenyl" as used herein encompasses all possible isomeric phenyl radicals optionally monosubstituted or disubstituted with a substituent selected from the group consisting of lower alkyl, lower alkoxy, and halo.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"RS-15385-197" refers to the selective $\alpha_2$-adrenoceptor antagonist (8aR,12aS,13aS)-3-methoxy-12-methanesulfonyl-5,6,8a,9,10,11,12,12a,13,13a-decahydro-8H-isoquino[2,1g][1,6]-naphthyridine hydrochloride.

"[$^3$H]-idazoxan" refers to tritiated idazoxan, named as (1,4-[6,7-$^3$H]-benzodioxan-2-yl)-2-imidazoline hydrochloride, or [$^3$H]-RX 781094. It is available from, i.a., Amersham plc.

"Masking concentration" as used herein means the concentration of a compound known to block or occlude the total population of a particular site for which the compound has affinity. For example, the masking concentration of a selective $\alpha_2$-adrenoceptor antagonist refers to the concentration of that compound known to block or occlude the total population of $\alpha_2$-adrenoceptor sites present in the tissue under examination.

"Optional" or "optionally" means that the subsequently described event or circumstance may or may not occur, and that the description includes instances where said event or circumstance occurs and instances in which it does not. For example, "optionally substituted phenyl" means that phenyl may or may not be substituted with a substituent selected from the group consisting of lower alkyl, lower alkoxy, hydroxy, nitro, trifluoromethyl and halo, and encompasses unsubstituted phenyl and all possible isomeric phenyl radicals that are mono, di or trisubstituted.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "disease state which is alleviable by treatment with a compound having high selectivity and affinity for the imidazoline receptor site" as used herein is intended to cover all disease states which are generally acknowledged in the art to be usefully treated with compounds having high selectivity and affinity for the imidazoline site in general, and those disease states which have been found to be usefully treated by the specific compounds of our invention, the compounds of Formula (I). Such disease states include, but are not limited to, cerebral ischemia, hypertension, excessive intraocular pressure, parkinsonian disorders, eating disorders, seasonal affective disorders, panic disorders, urinary incontinence, diuresis, fertility disorders (including the treatment of infertility by, for example, in vitro fertilization, and use in antifertility), sexual dysfunction, impotence, postnatal depression, mild stress-induced amenorrhoea, and galactorrhoea.

The compounds of Formula (I), illustrated below, will be named using the indicated numbering system:

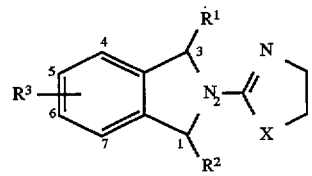

It should be understood that Formula (I) as drawn is intended to represent the racemic form of compounds of Formula (I) as well as the individual enantiomers and non-racemic mixtures thereof, although for the sake of clarity only one enantiomer is shown. The scope of the invention as described and claimed encompasses the racemic forms of the compounds of Formula (I) as well as the individual enantiomers and non-racemic mixtures thereof.

The compounds of Formula (I) where X is sulfur are thiazoline derivatives, and are illustrated below as Formula (IA):

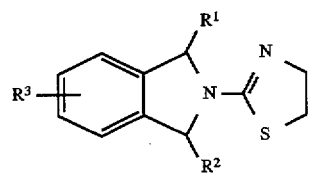

Following are examples of how representative compounds of Formula (IA) are named:

A compound of Formula (IA) wherein $R^1$ and $R^2$ are hydrogen and $R^3$ is 4-chloro is named:

4-chloro-2-(thiazolin-2-yl)isoindoline.

A compound of Formula (IA) wherein $R^1$ is hydrogen, $R^2$ is methyl and $R^3$ is 5-trifluoromethyl is named:

3-methyl-5-trifluoromethyl-2-(thiazolin-2-yl)isoindoline.

The compounds of Formula (I) where X is oxygen are oxazoline derivatives, and are illustrated below as Formula (IB):

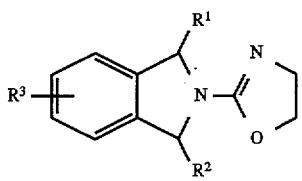

(IB)

Following are examples of how representative compounds of Formula (IB) are named.

A compound of Formula (IB) wherein $R^1$ and $R^2$ are hydrogen and $R^3$ is 4-chloro is named:

4-chloro-2-(oxazolin-2-yl)isoindoline.

A compound of Formula (IB) wherein $R^1$ is hydrogen, $R^2$ is ethyl and $R^3$ is 6-methoxy is named:

3-ethyl-6-methoxy-2-(oxazolin-2-yl)isoindoline.

The compounds of Formula (I) where X is —NH— are imidazoline derivatives, and are illustrated below as Formula (IC):

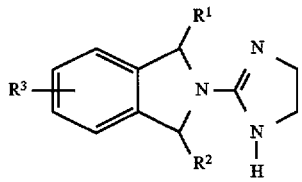

(IC)

Following are examples of how representative compounds of Formula (IC) are named.

A compound of Formula (IC) wherein $R^1$ and $R^2$ are hydrogen and $R^3$ is 4-chloro is named:

4-chloro-2-(imidazolin-2-yl) isoindoline.

A compound of Formula (IC) wherein $R^1$ is methyl, $R^2$ is ethyl and $R^3$ is 7-amino is named:

1-methyl-3-ethyl-7-amino-2-(imidazolin-2-yl) isoindoline.

PREFERRED EMBODIMENTS

Among the family of compounds of the present invention, a preferred group includes the compounds of Formula (I) in which X is oxygen, especially where $R^1$ and $R^2$ are hydrogen. Within this category a preferred group includes the compounds where $R^3$ is halo, especially chloro, more especially 4-chloro.

Another preferred category includes the compounds of Formula (I) in which X is sulfur, especially where $R^1$ and $R^2$ are hydrogen. Within this category a preferred group includes the compounds where $R^3$ is halo, especially chloro, more especially 5-chloro.

A third preferred category includes the compounds of Formula (I) in which X is —NH—, especially where $R^1$ and $R^2$ are hydrogen. Within this category a preferred group includes the compounds where $R^3$ is halo, especially chloro, more especially 4-chloro.

At present, the most preferred compounds are:

5-chloro-2-(oxazolin-2-yl)isoindoline;
4-chloro-2-(thiazolin-2-yl) isoindoline; and
4-chloro-2-(imidazolin-2-yl)isoindoline.

METHODS OF PREPARATION

Preparation of Compounds of Formula (2)

The compounds of Formula (I) may be prepared from the intermediates of Formula (2):

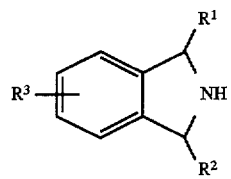

(2)

where $R^1$, $R^2$ and $R^3$ are as defined in the Summary of the Invention.

The preparation of compounds of Formula (2) where $R^1$ and $R^2$ are hydrogen (designated as Formula (2a)), and the preparation of compounds of Formula (2) where at least one of $R^1$ and $R^2$ is lower alkyl (designated as Formula (2b)) is illustrated below in Reaction Scheme IA.

REACTION SCHEME IA

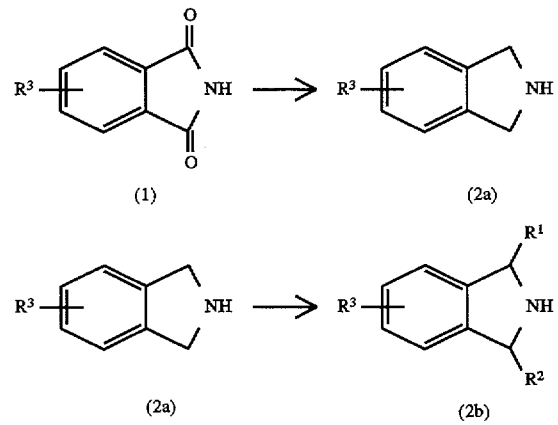

Preparation of Compounds of Formula (2a)

The intermediate of Formula (1) is obtained commercially, or may be prepared according to the method disclosed in Org. Synthesis, Coll. Vol. 1, p457. To prepare compounds of Formula (2a), a compound of Formula (1) is reacted with an excess of a suitable reducing agent (for example, borane, or borane/dimethylsulfide complex, preferably borane/dimethylsulfide complex). The reaction is preferably carried out in an ethereal solvent (for example diethyl ether, dimethoxyethane, dioxane or tetrahydrofuran, preferably tetrahydrofuran), at a temperature of about 40° C. to 100° C., preferably at about the reflux temperature of the solvent, for about 8 to 24 hours, preferably about 18 hours. The reaction is then quenched with an acid, preferably hydrochloric acid, and the mixture refluxed for a further 1–4 hours, preferably about 2 hours. The product of Formula (2a), an isoindoline derivative, is isolated by conventional means, and preferably purified by distillation.

Preparation of Compounds of Formula (2b)

Compounds of Formula (2b) are prepared from compounds of Formula (2a) by α-alkylation, as disclosed in J. Org. Chem., Vol. 53, pp 5381–5383 (1988), the complete disclosure of which is hereby incorporated by reference.

Preparation of Compounds of Formula (3)

Compounds of Formula (IB) may also be prepared from the intermediates of Formula (3), the preparation of which is illustrated below in Reaction Scheme IB.

REACTION SCHEME IB

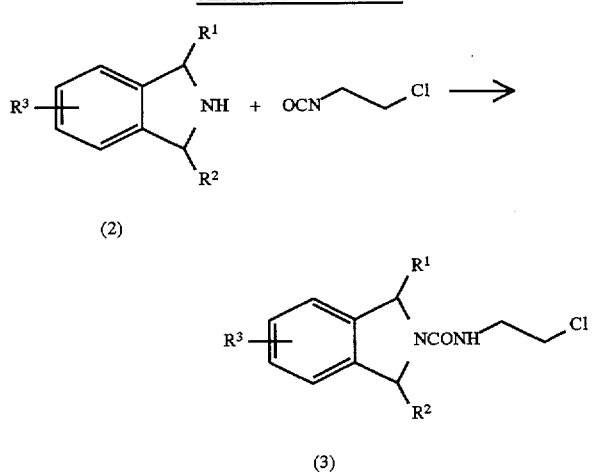

To prepare compounds of Formula (3), a compound of Formula (2) is reacted with about 1 to 1.5 molar equivalents, preferably about 1.1 molar equivalents, of 2-chloroethylisocyanate. The reaction is preferably carried out in an ethereal solvent (for example diethyl ether, dimethoxyethane, dioxane or tetrahydrofuran, preferably tetrahydrofuran), at a temperature of about −10° C. to 10° C. preferably at about 0° C., for about 10 minutes to 4 hours, preferably about 1 hour. The product of Formula (3), a 2-chloroethylamidoisoindoline derivative, is isolated by conventional means.

Preparation of Compounds of Formula (I)

The compounds of Formula (I) are prepared from the compounds of Formula (2) as illustrated below in Reaction Scheme II.

REACTION SCHEME II

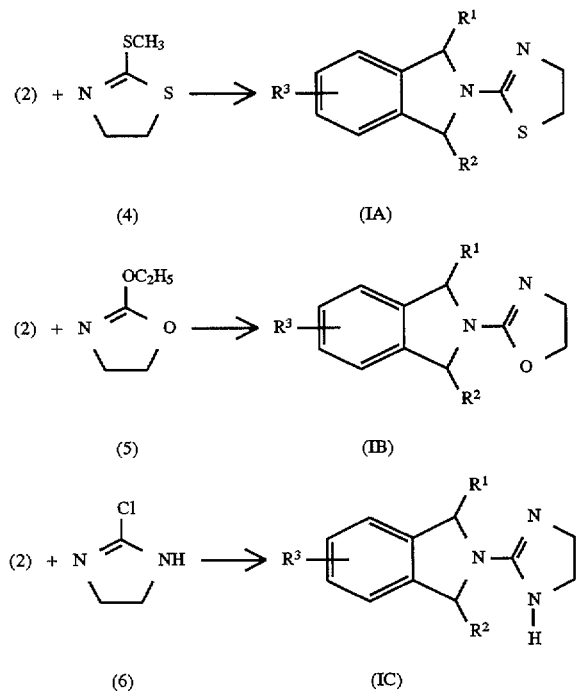

Compounds of Formula (IA)

To prepare compounds of Formula (IA), a compound of Formula (2) is reacted with about 1 to 1.5 molar equivalents, preferably about 1 molar equivalent, of 2-methylthio-2-thiazoline, the compound of Formula (4), in the presence of a catalytic amount of an acid, preferably a sulfonic acid, most preferably β-naphthylsulfonic acid. The reaction is preferably carried out in the absence of any solvent, at a temperature of about 100° C. to 180° C., preferably at about 150° C., for about 10 minutes to 2 hours, preferably about 30 minutes. The product of Formula (IA), a 2-(thiazolin-2-yl)isoindoline derivative, is isolated and purified by conventional means, preferably chromatography followed by crystallization of an acid addition salt.

Compounds of Formula (IB)

To prepare compounds of Formula (IB), a compound of Formula (2) is reacted with about 1 to 1.5 molar equivalents, preferably about 1.2 molar equivalents, of 2-ethoxy-2-oxazoline, the compound of Formula (5), in the presence of a catalytic amount of an acid, preferably a sulfonic acid, most preferably β-naphthylsulfonic acid. The reaction is carried out in an inert solvent, preferably an aromatic solvent, most preferably toluene, at a temperature of about 70°–140° C., preferably at about 100° C., for about 30 minutes to 4 hours, preferably about 1 hour. The product of Formula (IB), a 2-(oxazolin-2-yl)isoindoline derivative, is isolated and purified by conventional means, preferably chromatography followed by crystallization of an acid addition salt.

Compounds of Formula (IC)

To prepare compounds of Formula (IC), a compound of Formula (2) is reacted with about 1 to 2.0 molar equivalents, preferably about 1.5 molar equivalents, of 2-chloro-2-imidazoline, the compound of Formula (6). The reaction is carried out in an inert solvent, preferably a protic solvent, most preferably isopropanol, at a temperature of about 50°–100° C., preferably at about 80° C., for about 30 minutes to 4 hours, preferably about 1.5 hours. The product of Formula (IC), a 2-(imidazolin-2-yl)isoindoline hydrochloride salt, is isolated and purified by conventional means, preferably crystallization of the salt.

Alternative Preparation of Compounds of Formula (IB)

Compounds of Formula (IB) may also be prepared as shown in Reaction Scheme III below.

REACTION SCHEME III

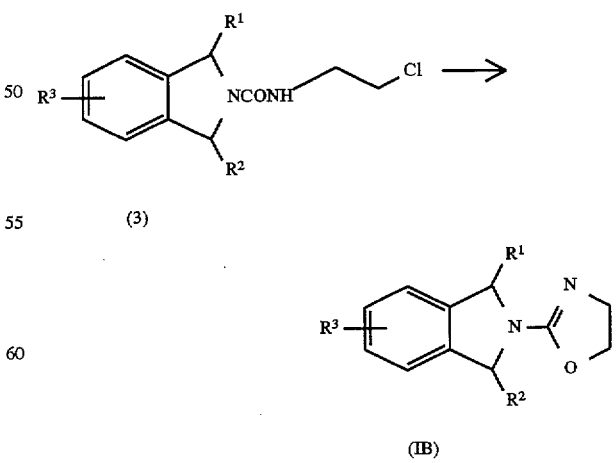

To prepare compounds of Formula (IB), a compound of Formula (3) is cyclized in an inert solvent, preferably a protic solvent, most preferably water, at a temperature of about 50°–100° C., preferably at about 100° C., for about 30 minutes to 4 hours, preferably about 2 hours. The product of Formula (IC), a 2-(oxazolin-2-yl) isoindoline salt, is isolated and purified by conventional means, preferably crystallization of an acid addition salt.

Isolation and purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples hereinbelow. However, other equivalent separation or isolation procedures could, of course, also be used.

Salts of Compounds of Formula (I)

The compounds of Formula (I) may be converted to a corresponding acid addition salt by virtue of the presence of the nitrogen atoms.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of Formula (I) may be converted to the corresponding free bases by treatment with at least a stoichiometric amount of a suitable base such as sodium or potassium hydroxide, potassium carbonate, sodium bicarbonate, ammonia, and the like.

PREFERRED PROCESSES

In summary, the compounds of the present invention are made according to the following last steps:

1. A process for preparing compounds of Formula (I), wherein:

$R^1$ and $R^2$ are independently hydrogen or lower alkyl;
   $R^3$ is hydrogen, lower alkyl, lower alkoxy, hydroxy, halo, optionally substituted phenyl, amino, nitro or trifluoromethyl; and
   X is —S—;
   comprises:
   reacting a compound of the formula:

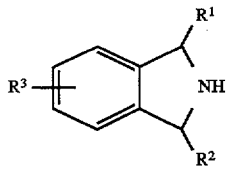

where $R^1$, $R^2$ and $R^3$ are as defined in the Summary of the Invention;
with 2-methylthio-2-thiazoline.

2. A process for preparing compounds of Formula (I), wherein:

$R^1$ and $R^2$ are independently hydrogen or lower alkyl;
   $R^3$ is hydrogen, lower alkyl, lower alkoxy, hydroxy, halo, optionally substituted phenyl, amino, nitro or trifluoromethyl; and
   X is —O—;
   comprises:
   reacting a compound of the formula:

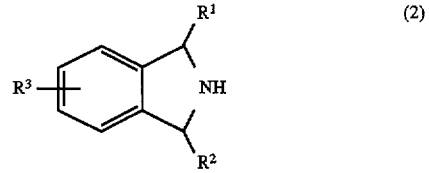

where $R^1$, $R^2$ and $R^3$ are as defined in the Summary of the Invention;
with 2-ethoxy-2-oxazoline.

3. Alternatively, a process for preparing compounds of Formula (I), wherein:

$R^1$ and $R^2$ are independently hydrogen or lower alkyl;
   $R^3$ is hydrogen, lower alkyl, lower alkoxy, hydroxy, halo, optionally substituted phenyl, amino, nitro or trifluoromethyl; and
   X is —O—;
   comprises:
   cyclizing a compound of the formula:

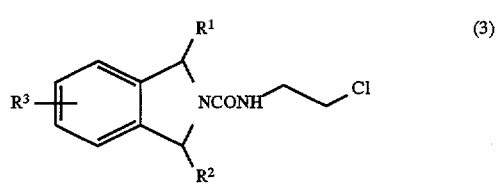

where $R^1$, $R^2$ and $R^3$ are as defined in the Summary of the Invention.

4. A process for preparing compounds of Formula (I), wherein:

$R^1$ and $R^2$ are independently hydrogen or lower alkyl;
   $R^3$ is hydrogen, lower alkyl, lower alkoxy, hydroxy, halo, optionally substituted phenyl, amino, nitro or trifluoromethyl; and
   X is —NH—;
   comprises:
   reacting a compound of the formula:

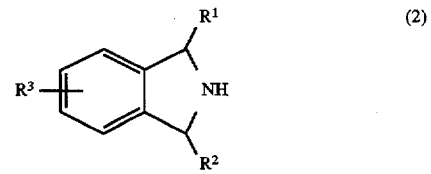

where $R^1$, $R^2$ and $R^3$ are as defined in the Summary of the Invention;
with 2-chloro-2-imidazoline.

6. Alternatively, a process for preparing compounds of Formula (I), wherein $R^1$, $R^2$ and $R^3$ are as defined in the Summary of the Invention, constitutes:

(a) reacting the compound of Formula (I) with an acid to give a pharmaceutically acceptable acid addition salt; or (b) reacting an acid addition salt of a compound of Formula (I) with a base to give the corresponding free base; or (c) converting an acid addition salt of a compound of Formula (I) to another pharmaceutically acceptable acid addition salt of Formula (I).

Utility and Administration:

General Utility

The compounds of Formula (I) and the pharmaceutically acceptable acid addition salts thereof have been found to possess valuable pharmacological properties, and, in particular, have been shown to have high selectivity and high affinity for imidazoline sites in laboratory tests. Accordingly these compounds and pharmaceutically acceptable compositions containing them are useful in the regulation of physiological phenomena related to imidazoline sites, including cerebral ischemia, hypertension, excessive intraocular pressure, parkinsonian disorders, eating disorders, seasonal affective disorders, panic disorders, urinary incontinence, diuresis, fertility disorders (including the treatment of infertility by, for example, in vitro fertilization, and use in antifertility), sexual dysfunction, impotence, postnatal depression, mild stress-induced amenorrhoea, and galactorrhoea. The compounds of Formula (I) are particularly useful for modification of the female reproductive cycle.

Testing

Potential for high selectivity and high affinity for imidazoline sites is determined in vitro by a modification of the method of Brown et al., *Br. J. Pharmacology*, Vol. 99, pp 481∝486 (1990), as described in Example 11.

Lowering of intraocular pressure is shown in vivo by the method of Moses, R. A., *Tr. Am. Acad. Opth. and Otol.*, January–February 1962: 88–95.

Potential for treatment of cerebral ischemia is shown in vitro by a modification of the method of Gotti et al., *Brain Res.*, Vol 522(2), pp 290–307 (1990).

The antihypertensive activity of the compounds may be determined in conscious spontaneous hypertensive rats prepared with indwelling arterial catheter by the in vivo assay described in Popovic V. and Popovic P., *J. Applied. Physiol.*, Vol. 15, pp. 727–728 (1960), or a modification thereof.

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula (I) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dose for oral, parenteral and otherwise systemic routes of administration is in the range of 0.01–20 mg/kg/day, preferably 0.1–10 mg/kg/day. For an average 70 kg human, this would amount to 0.7–1400 mg per day, or preferably 7–700 mg/day.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of Formula (I) or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%–95% active ingredient, more preferably 2–50%, most preferably 5–8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1% to 10%, most preferably 0.5% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.5% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

The following preparation and examples illustrate the invention but are not intended to limit its scope.

PREPARATION 1

Preparation of a Compound of Formula (2a)

A. Preparation of (2a) where $R^3$ is 4-chloro

To a solution of 4-chlorophthalimide (60 g) in 1 liter of tetrahydrofuran was added borane-methyl sulfide complex (100 ml of 10M), and the mixture was refluxed overnight. After cooling, 100 ml of 6N hydrochloric acid was added slowly, the mixture refluxed for 2 hours, and then filtered. The filtrate was concentrated under reduced pressure, and the resulting aqueous solution washed with ethyl acetate. The aqueous layer was then basified with ammonium hydroxide and extracted with methylene chloride. Solvent was removed from the extract, and the residue distilled under vacuum to give 4-chloroisoindoline, a white solid, m.p. 48°–50° C.

B. Preparation of (2a) varying $R^3$

Similarly, replacing 4-chlorophthalimide with:

phthalimide;

5-chlorophthalimide; and 4-fluorophthalimide;

and following the procedures of Preparation 1A above, the following compounds of Formula (2a) were prepared:

isoindoline;

5-chloroisoindoline; and 4-fluoroisoindoline.

C. Preparation of (2a) varying $R^3$

Similarly, replacing 4-chlorophthalimide with other compounds of Formula (1), and following the procedures of Preparation 1A above, the following exemplary compounds of Formula (2a) are prepared:

3-methylisoindoline;

4-methoxyisoindoline;

5-phenylisoindoline; and 4-trifluoromethylisoindoline;

PREPARATION 2

Preparation of a Compound of Formula (3)

A. Preparation of (3) where $R^1$ and $R^2$ are hydrogen, and $R^3$ is 4-chloro

To a solution of 2-chloroethylisocyanate (0.93 ml) in tetrahydrofuran (50 ml) at 0° C. was added 4-chloroisoindoline (1.53 g), and the mixture stirred at 0° C. for 1 hour. The solvent was removed under reduced pressure, and the residue triturated with ether, giving 2-(2-chloroethylamido)-4-chloroisoindoline, a compound of Formula (3), as a white solid, m.p. 151° C.

B. Preparation of (3) varying $R^1$, $R^2$ and $R^3$

Similarly, replacing 4-chloroisoindoline with other compounds of Formula (2), and following the procedures of Preparation 2A above, the following exemplary compounds of Formula (3) are prepared:

2-(2-chloroethylamido)isoindoline;

2-(2-chloroethylamido)-3-chloroisoindoline;

2-(2-chloroethylamido)-4-fluoroisoindoline;

2-(2-chloroethylamido)-3-methylisoindoline;

2-(2-chloroethylamido)-4-methoxyisoindoline;

2-(2-chloroethylamido)-5-phenylisoindoline; and 2-(2-chloroethylamido)-4-trifluoromethylisoindoline.

EXAMPLE 1

Preparation of Compounds of Formula (IA)

A. Preparation of (IA) where $R^1$ and $R^2$ are hydrogen, and $R^3$ is 4-chloro A mixture of 4-chloroisoindoline (700 mg), 2-methylthio-2-thiazoline (600 mg), and β-naphthylsulfonic acid (35 mg) was heated at 150° C. for 30 minutes. The product was cooled, dissolved in methylene chloride, washed with water, the organic layer dried over anhydrous potassium carbonate, filtered, and solvent removed from the filtrate under reduced pressure. The residue was chromatographed on silica gel packed in methylene chloride/2% methanol/ammonia, eluting with methylene chloride/2% methanol, to give 4-chloro-2-(thiazolin-2-yl)isoindoline, a compound of Formula (IA), m.p. 167°–169° C.

15

The solid was dissolved in acetone, and a solution of ethanol/hydrochloric acid added, to give 4-chloro-2-(thiazolin-2-yl)isoindoline hydrochloride, a compound of Formula (IA), m.p. 287°–288° C.

B. Preparation of (IA) where $R^1$, $R^2$ and $R^3$ are hydrogen

Similarly, replacing 4-chloroisoindoline with isoindoline, and following the procedures of Example 1A above, the following compounds of Formula (IA) were prepared:

2-(thiazolin-2-yl)isoindoline, m.p. 125°–128° C.; and 2-(thiazolin-2-yl) isoindoline hydrochloride, m.p. 243-245° C.

C. Preparation of (IA) varying $R^1$, $R^2$ and $R^3$

Similarly, replacing 4-chloroisoindoline with other compounds of Formula (2), and following the procedures of Example 1A above, the following compounds of Formula (IA) are prepared:

3-chloro-2-(thiazolin-2-yl)isoindoline;

4-fluoro-2-(thiazolin-2-yl) isoindoline;

3-methyl-2-(thiazolin-2-yl) isoindoline;

4-methoxy-2-(thiazolin-2-yl)isoindoline;

5-phenyl-2-(thiazolin-2-yl)isoindoline;

3-chloro-2-(thiazolin-2-yl)isoindoline; and 4-trifluoromethyl-2-(thiazolin-2-yl)isoindoline.

EXAMPLE 2

Preparation of Compounds of Formula (IB)

A. Preparation of (IB) where $R^1$ and $R^2$ are hydrogen, and $R^3$ is 4-fluoro A mixture of 4-fluoroisoindoline (400 mg), 2-ethoxy-2-oxazoline (400 mg), and β-naphthylsulfonic acid (30 mg) in 50 ml of toluene was stirred at 100° C. for 1 hour. The solvent as removed under reduced pressure, and the residue chromatographed on silica gel, eluting with 1–4% methanol in ethyl acetate, to give 4-fluoro-2-(oxazolin-2-yl) isoindoline, a compound of Formula (IB), m.p. 125°–129° C.

The solid was dissolved in ethanol, and a solution of ether/hydrochloric acid added, to give 4-fluoro-2-(oxazolin-2-yl)isoindoline hydrochloride, m.p. 183°–184° C.

B. Preparation of (IB) where $R^1$ and $R^2$ are hydrogen and $R^3$ is 3-chloro

Similarly, replacing 4-fluoroisoindoline with 3-chloroisoindoline, and following the procedures of Example 2A above, the following compounds of Formula (IB) were prepared:

5-chloro-2-(oxazolin-2-yl)isoindoline; and 5-chloro-2-(oxazolin-2-yl)isoindoline hydrochloride m.p. 187°–188° C.

C. Preparation of (IB) varying $R^1$, $R^2$ and $R^3$

Similarly, replacing 4-fluoroisoindoline with other compounds of Formula (2), and following the procedures of Example 2A above, the following compounds of Formula (IB) are prepared:

3-chloro-2-(oxazolin-2-yl)isoindoline;

4-fluoro-2-(oxazolin-2-yl) isoindoline;

3-methyl-2-(oxazolin-2-yl)isoindoline;

4-methoxy-2-(oxazolin-2-yl) isoindoline;

5-phenyl-2-(oxazolin-2-yl)isoindoline;

3-chloro-2-(oxazolin-2-yl)isoindoline; and 4-trifluoromethyl-2- (oxazolin-2-yl) isoindoline.

EXAMPLE 3

Alternative Preparation of Compounds of Formula (IB)

A. Preparation of (IB) where $R^1$ and $R^2$ are hydrogen and $R^3$ is 4-chloro

A mixture of 2-(2-chloroethylamido)-4-chloroisoindoline (1.75 g) suspended in water (100 ml) was heated to reflux. After 2 hours the solid had all dissolved. The solution was cooled, washed with ethyl acetate, and the aqueous layer made basic with ammonia. The precipitated solid was extracted into methylene chloride, dried over magnesium sulfate, filtered, and the filtrate evaporated to 4-chloro-2-(oxazolin-2-yl)isoindoline, a compound of Formula (IB), which was converted into its hydrochloride salt using anhydrous ethanol/ether/hydrochloric acid solution, m.p. 152°–153° C.

B. Preparation of (IB) where $R^1$, $R^2$ and $R^3$ are hydrogen

Similarly, replacing 4-chloroisoindoline with isoindoline, and following the procedures of Example 3A above, the following compounds of Formula (IB) were prepared:

2-(oxazolin-2-yl)isoindoline, m.p. 134°–134.5° C.; and 2-(oxazolin-2-yl)isoindoline hydrochloride, m.p. 201°–202° C.

C. Preparation of (IB) varying $R^1$, $R^2$ and $R^3$

Similarly, replacing 4-chloroisoindoline with other compounds of Formula (2), and following the procedures of Example 3A above, the following compounds of Formula (IB) are prepared:

3-chloro-2-(oxazolin-2-yl)isoindoline;

4-fluoro-2-(oxazolin-2-yl)isoindoline;

3-methyl-2-(oxazolin-2-yl)isoindoline;

4-methoxy-2-(oxazolin-2-yl)isoindoline;

5-phenyl-2-(oxazolin-2-yl)isoindoline;

3-chloro-2-(oxazolin-2-yl) isoindoline; and 4-trifluoromethyl-2-(oxazolin-2-yl)isoindoline.

EXAMPLE 4

Preparation of Compounds of Formula (IC)

A. Preparation of (IC) where $R^1$ and $R^2$ are hydrogen and $R^3$ is 4-chloro 2-Chloroimidazoline sulfate (3.0 g) was partitioned between excess cold 5% sodium hydroxide saturated with sodium chloride and ether. The aqueous layer was extracted twice more with ether, and the combined organic layers dried over sodium sulfate. The ether solution was added to a solution of 4-chloroisoindoline (1.53 g) in 25 ml of isopropanol, the ether removed under reduced pressure, and the remaining isopropanol solution refluxed for 1½ hours. The precipitated solid was filtered off and recrystallized from hot ether/ethanol, to give 4-chloro-2-(imidazolin-2-yl)isoindoline hydrochloride, a compound of Formula (IC), m.p. 272°–275° C.

B. Preparation of (IC) where $R^1$ and $R^2$ are hydrogen and $R^3$ is hydrogen or 5-chloro Similarly, replacing 4-chloroisoindoline with isoindoline or 5-chloroisoindoline, and following the procedures of Example 4A above, the following compounds of Formula (IC) were prepared:

2-(imidazolin-2-yl)isoindoline hydrochloride, m.p. 298°–300° C.; and 5-chloro-2-(imidazolin-2-yl)isoindoline hydrochloride, m.p. 262°–263° C.

17

C. Preparation of (IC) varying $R^1$, $R^2$ and $R^3$

Similarly, replacing 4-chloroisoindoline with other compounds of Formula (2), and following the procedures of Example 4A above, the following compounds of Formula (IC) are prepared:

3-chloro-2-(imidazolin-2-yl)isoindoline;
4-fluoro-2-(imidazolin-2-yl)isoindoline;
3-methyl-2-(imidazolin-2-yl)isoindoline;
4-methoxy-2-(imidazolin-2-yl)isoindoline;
5-phenyl-2-(imidazolin-2-yl)isoindoline;
3-chloro-2-(imidazolin-2-yl) isoindoline; and
4-trifluoromethyl-2-(imidazolin-2-yl)isoindoline.

In Examples 5 through 10 the active ingredient is 4-chloro-2-(imidazolin-2-yl)isoindoline, and a daily dose of 20 mg is assumed. Other compounds of Formula (I) or a pharmaceutically acceptable salt thereof at the same or different dosage may be substituted therein.

EXAMPLE 5

Composition for Oral Administration

| The composition contains: | % wt./wt. |
| --- | --- |
| Active ingredient | 20% |
| Lactose | 79.5% |
| Magnesian stearate | 0.5% |

The two ingredients are mixed and dispensed into capsules containing 100 mg each; one capsule would approximate a total daily dosage.

EXAMPLE 6

Composition for Oral Administration

| The composition contains: | % wt. /wt. |
| --- | --- |
| Active ingredient | 50.0% |
| Magnesium stearate | 0.5% |
| Crosscarmellose sodium | 2.0% |
| Lactose | 46.5% |
| PVP (polyvinylpyrrolidine) | 1.0% |

The above ingredients are combined and granulated using methanol as solvent. The formulation is then dried and formed into tablets (containing 20 mg of active compound) with an appropriate tableting machine.

EXAMPLE 7

Parenteral Formulation (IV)

| The composition contains: | % wt./wt. |
| --- | --- |
| Active ingredient | 7.0 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

18

EXAMPLE 8

Suppository Formulation

| The composition contains: | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 9

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 10

Composition for Topical Administration to the Eye

| The composition contains: | % wt/vol |
| --- | --- |
| Active ingredient | 0.50 |
| Benzalkonium chloride | 0.02 |
| EDTA | 0.01 |
| Phenylethanol | 0.25 |
| Boric acid | 1.62 to adjust pH |
| and water qs | 100 ml |

The first four ingredients are dissolved in less than the required total volume of water, and the pH adjusted to 7.4. The volume is then brought to 100 ml with additional water.

EXAMPLE 11

Determination of Affinity at Imidazoline Receptors
[$^3$H]-Idazoxan Binding

Membranes (300–500 µg, from prewashed rat cortex or rabbit kidney prepared by homogenization and centrifugation in Tris HCl buffer) are incubated with 1 nM [$^3$H]-idazoxan for 90 minutes at 25° C. in the presence of 0.1 µM of a selective $\alpha_2$-adrenoceptor antagonist (RS-15385-197) and various concentrations of the test compound of Formula (I) in a final volume of 0.5 ml assay buffer (50 mM Tris HCl, pH 7.4, containing 0.5 mM of EDTA). Bound ligand is separated from free ligand by filtration followed by two 5 second washes with assay buffer at room temperature. Non-specific binding is determined in the presence of a saturating concentration (1 µM) of cirazoline. The affinity of the test compound for the imidazoline site and for other receptor systems ($\alpha_1$ and $\alpha_2$-adrenergic, $\beta_1$ and $\beta_2$-adrenergic, $5HT_{1A}$, $5HT_2$, dopamine$_1$ and dopamine$_2$, muscarinic$_1$ and muscaranic$_2$ receptors, and dihydropyridine binding site on calcium channels) was compared as $pK_i$ values.

The compounds of Formula (I) show high selectivity for the imidazoline site.

EXAMPLE 12

Determination of Effects on the Oestrus Cycle

Mature cycling female Sprague-Dawley rats were dosed either with test compound (1 mg/Kg s.c.) or water twice daily (9 a.m. and 4 p.m.) for 16 days. A vaginal smear was taken every day during the study and stained with Shorr's stain (described below):

Shorr's stain contains:

| | |
|---|---|
| 50% ethanol | 100 ml |
| Biebrich scarlet | 0.5 g |
| Orange G | 0.25 g |
| Fast Green | 0.075 g |
| Phosphotungstic acid | 0.5 g |
| Phosphomolybdic acid | 0.5 g |
| Glacial acetic acid | 1 ml |

A smear was taken, wet-fixed in 95% ethanol, and stained in the above solution for 1 minute. Slides were then taken through 70%, 95% and absolute ethanol, dipping slides into each solution 10 times, then cleared in xylene and the slides mounted.

A disruption in the oestrus cycle was seen for compounds of Formula (I).

EXAMPLE 13

Determination of Effects on Ovulation Induction in the Pseudopregnant Rat

Mature cycling female Sprague-Dawley rats were made pseudopregnant at midday on the day of oestrus. Six of these animals were dosed with test compound (5 mg/Kg p.o. b.i.d. from days 1–8), six with water, and smears were taken on all animals over the next 13 days.

Early return to oestrus was seen with the compounds of Formula (I).

EXAMPLE 14

Determination of Effects on Plasma Prolactin Levels in the Male Rat

Male rats were dosed with either test compound (1 mg/Kg s.c.) or water, b.i.d. for 14 days, and blood samples were taken 2 hours later. The compounds of Formula (I) reduced prolactin levels in the male rat.

EXAMPLE 15

Determination of Antihypertensive Activity (In Vivo Assay)

The antihypertensive effects of the compounds of formula (I) are evaluated in spontaneously hypertensive rats (Iffa Credo, aged 18–20 weeks)). The rats are anesthetized with pentobarbital (50 mg/Kg i.p.), and a catheter implanted into the descending aorta via a femoral artery. The catheter is exteriorized at the back of the neck and sealed with a pin. After surgery the rats are housed in individual cages, and pulsatile aortic blood pressure measured directly 1–3 days later in groups of 4–8 conscious animals, using a Statham P50 pressure transducer connected to a Gould S8000 chart recorder. Heart rate is determined by using the pulse pressure to trigger a ratemeter. Rats with mean blood pressure greater than 145 mm Hg are considered to be hypertensive.

The test compounds are suspended in 2% Tween 80 vehicle for oral administration. A control group receives vehicle (0.5 ml/Kg p.o.) alone. Cardiovascular parameters are recorded at 15, 30, 45 and 60 minutes, and thereafter at hourly intervals for the first 7 hours, then at 24 hours post dosing. Maximum changes in systolic, diastolic and mean blood pressure are measured, as are changes in heart rate. Calculations are made of the percentage changes in blood pressure and heart rate with respect to the initial values and vehicle-treated time controls. The duration of the antihypertensive effect is calculated as the time during which the blood pressure value remains significantly lower than the vehicle-treated group. The compounds of formula (I) demonstrate positive antihypertensive activity in this assay.

EXAMPLE 16

Method for Assaying Imidazoline Receptors Using Tritiated Test Compound

Protocol:

Washed rat kidney membranes were prepared as described in Example 11 for [$^3$H]-idazoxan, and incubated with 1 nM of tritiated test compound, for example [$^3$H]-4-chloro-2-(imidazolin-2-yl)isoindoline, and various concentrations of the compound being tested for imidazoline receptor binding activity, in a final volume of 0.5 ml assay buffer (50 mM Tris HCl, pH 7.4, containing 0.5 mM EDTA). Bound ligand is separated from free ligand as described in Example 11 for [$^3$H]-idazoxan binding. Non-specific binding is defined with 10 µM cirazoline.

EXAMPLE 17

Study of the Distribution of Imidazoline Receptors in Rat Brain using [$^3$H]-Idazoxan Frozen sections (20 µm) of rat brain are prepared and mounted onto glass slides. Sections are preincubated for 20 minutes at room temperature in assay buffer (170 mM Tris HCl, pH 7.4, containing 0.5 mM EDTA, 100 µM phenylmethylsulfonyl fluoride, and 0.1 µM RS-15385-197). Incubations are carried out in assay buffer containing 3 nM [$^3$H]-idazoxan for 3 hours at room temperature. Parallel sections are incubated with 1 µM cirazoline to define non-specific binding. Sections are washed in ice-cold assay buffer for 10 minutes, then dipped in ice-cold distilled water and dried. Labelled sections are opposed to $^3$[H]-sensitive Hyperfilm (Amersham plc) for 12 weeks. The density of sites in each brain region is measured using a Quantimet 970 image analysis system.

This methodology demonstrates that imidazoline binding sites are located in key areas associated with the control of mood and modulation of hormone release, particularly for those hormones responsible for modulation of the oestrus cycle.

While the present invention has been described with reference to the specific embodiments thereof, it should be understood by those skilled in the art that various changes may be made and equivalents may be substituted without

What is claimed is:

1. A compound of the formula:

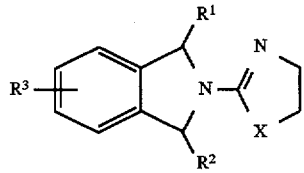

wherein:
R$^1$ and R$^2$ are independently hydrogen or lower alkyl;
R$^3$ is hydrogen, lower alkyl, lower alkoxy, hydroxy, halo, amino, nitro or trifluoromethyl; and
X is —NH—, —O— or —S—;
or a pharmaceutically acceptable salt thereof.

2. The compound of claim 1 wherein X is oxygen, or a pharmaceutically acceptable salt thereof.

3. The compound of claim 2 wherein R$^1$ and R$^2$ are hydrogen, or a pharmaceutically acceptable salt thereof.

4. The compound of claim 3 wherein R$^3$ is halo, or a pharmaceutically acceptable salt thereof.

5. The compound of claim 4 wherein R$^3$ is 5-chloro, namely 5-chloro-2-(oxazolin-2-yl)isoindoline, or a pharmaceutically acceptable salt thereof.

6. The compound of claim 1 wherein X is sulfur, or a pharmaceutically acceptable salt thereof.

7. The compound of claim 6 wherein R$^1$ and R$^2$ are hydrogen, or a pharmaceutically acceptable salt thereof.

8. The compound of claim 7 wherein R$^3$ is halo, or a pharmaceutically acceptable salt thereof.

9. The compound of claim 8 wherein R$^3$ is 4-chloro, namely 4-chloro-2-(thiazolin-2-yl)isoindoline, or a pharmaceutically acceptable salt thereof.

10. The compound of claim 1 wherein X is —NH—, or a pharmaceutically acceptable salt thereof.

11. The compound of claim 10 wherein R$^1$ and R$^2$ are hydrogen, or a pharmaceutically acceptable salt thereof.

12. The compound of claim 11 wherein R$^3$ is halo, or a pharmaceutically acceptable salt thereof.

13. The compound of claim 12 wherein R$^3$ is 4-chloro, namely 4-chloro-2-(imidazolin-2-yl)isoindoline, or a pharmaceutically acceptable salt thereof.

14. A pharmaceutical composition comprising a therapeutically effective amount of a compound of claim 1, or a pharmaceutically acceptable salt thereof, in admixture with one or more pharmaceutically acceptable non-toxic carriers.

15. A method for treating a mammal having a disease state which is alleviable by treatment with a compound having high selectivity and affinity for the imidazoline receptor site, which comprises administering to a mammal in need thereof a therapeutically effective amount of a compound of claim 1, or a pharmaceutically acceptable salt thereof.

16. A method for assaying imidazoline receptor sites in isolated mammalian tissue preparations, which comprises contacting a compound of claim 1, or a pharmaceutically acceptable salt thereof, with said mammalian tissue preparation and [$^3$H]-idazoxan in the presence of a masking concentration of a selective $\alpha_2$-adrenoceptor antagonist, and determining the amount of the compound of claim 1 required to displace 50% of the [$^3$H]-idazoxan from the mammal tissue preparation.

17. The method of claim 16, wherein the selective $\alpha_2$-adrenoceptor antagonist is (8aR,12aS,13aS)-3-methoxy-12-methanesulfonyl-5,6,8a,9,10,11,12,12a,13,13a-decahydro-8H-isoquino[2,1g][1,6]naphthyridine hydrochloride.

18. The method of claim 17, wherein the compound of claim 1 is 4-chloro-2-(imidazolin-2-yl)isoindoline, or a pharmaceutically acceptable salt thereof.

* * * * *